US012698518B2

(12) United States Patent
Atrache et al.

(10) Patent No.: US 12,698,518 B2
(45) Date of Patent: Aug. 4, 2026

(54) PROCESS OF DIRECTLY DETECTING AND IDENTIFYING A MICROORGANISM IN A BIOLOGICAL SAMPLE DILUTED IN AN ENRICHMENT BROTH

(71) Applicant: BIOMERIEUX SA, Marcy l'Etoile (FR)

(72) Inventors: Vincent Atrache, Caluire (FR); Bruno Colin, Marcy l'Etoile (FR); Aurelie Lafay, Saint Laurent de Vaux (FR); Bouchra Makrouf, Lyons (FR); Pascal Montes, Sainte Consorce (FR); David Mosticone, Saint Consorce (FR); Jean-Claude Raymond, Bessenay (FR); Thierry Sofia, Marcy (FR); Antoine Vimont, Lyons (FR)

(73) Assignee: BIOMERIEUX SA, Marcy-l'Etoile (FR)

( * ) Notice: Subject to any disclaimer, the term of this patent is extended or adjusted under 35 U.S.C. 154(b) by 1631 days.

(21) Appl. No.: 17/123,726

(22) Filed: Dec. 16, 2020

(65) Prior Publication Data

US 2021/0102234 A1 Apr. 8, 2021

Related U.S. Application Data

(63) Continuation of application No. 13/808,485, filed as application No. PCT/FR2011/051624 on Jul. 7, 2011, now Pat. No. 10,907,190.

(30) Foreign Application Priority Data

Jul. 8, 2010 (FR) ...................................... 1055574

(51) Int. Cl.
*C12Q 1/04* (2006.01)
*G01N 33/02* (2006.01)
(Continued)

(52) U.S. Cl.
CPC ............... *C12Q 1/04* (2013.01); *G01N 33/02* (2013.01); *G01N 33/5438* (2013.01); *G01N 33/569* (2013.01)

(58) Field of Classification Search
CPC . C12Q 1/04; C12Q 1/00; G01N 33/02; G01N 33/5438; G01N 33/569;
(Continued)

(56) References Cited

U.S. PATENT DOCUMENTS 4,200,493 A 4/1980 Wilkins et al.
4,778,755 A 10/1988 Tsay et al.
(Continued)

FOREIGN PATENT DOCUMENTS

EP 0 446 972 A2 9/1991
WO 2009/122069 A1 10/2009

OTHER PUBLICATIONS

Stockwell (Meeting Abstracts—Abstracts of Paper Presented at the 2008 Pittsburgh Conference (Journal of Automated Methods and Management in Chemistry, vol. 2008, Article ID 502953, doi:10. 1155/2008/502953) (Year: 2008).*
(Continued)

*Primary Examiner* — Christopher L Chin
(74) *Attorney, Agent, or Firm* — Oliff PLC

(57) ABSTRACT

A process of detecting at least one microorganism present in a sample placed in a closed container. The process includes: a) placing said sample in contact in the container with a culture medium, a revealing system capable of allowing the detection, and a support capable of capturing the microorganism(s) to be detected, the support comprising magnetic particles, b) closing the container, c) placing the container under conditions capable of allowing growth of the microorganism(s), d) applying a magnetic field to the magnetic particles for bringing together the magnetic particles, and e)
(Continued)

detecting in real-time inside the closed container, using a detection means, the presence of the microorganism(s) fixed onto the capture support.

15 Claims, 8 Drawing Sheets

Specification includes a Sequence Listing.

(51) Int. Cl.
  *G01N 33/543*      (2006.01)
  *G01N 33/569*      (2006.01)
(58) Field of Classification Search
  CPC .... G01N 27/026; G01N 33/12; G01N 33/543; C12M 1/28
  USPC ........ 435/7.2, 7.32, 7.35, 7.37; 436/34, 164, 436/526, 805
  See application file for complete search history.

(56) References Cited

U.S. PATENT DOCUMENTS

| | | | |
|---|---|---|---|
| 5,795,773 | A | 8/1998 | Read et al. |
| 7,691,600 | B2 | 4/2010 | Mercader Badia et al. |
| 8,802,428 | B2 | 8/2014 | Koyama et al. |
| 9,902,987 | B2 * | 2/2018 | Raymond ................. C12C 1/00 |
| 2005/0254055 | A1 | 11/2005 | Peng |
| 2006/0216765 | A1 | 9/2006 | Grove et al. |
| 2007/0020720 | A1 | 1/2007 | Colin et al. |
| 2008/0152541 | A1 | 6/2008 | Mosticone et al. |
| 2008/0182272 | A1 | 7/2008 | Nagar et al. |
| 2009/0081766 | A1 | 3/2009 | Fukushima et al. |
| 2009/0218239 | A1 | 9/2009 | Gooding et al. |
| 2011/0020861 | A1 | 1/2011 | Colin et al. |
| 2014/0349280 | A1 | 11/2014 | Raymond et al. |
| 2015/0079597 | A1 | 3/2015 | Flandrois et al. |

OTHER PUBLICATIONS

Middlekauff et al., "Microbiology" ASBC Journal, vol. 39 No. 3, 1981.

Yang et al., "Electrical electrochemical impedance for rapid detection of foodborne pathogenic bacteria," Biotechnology Advances, 26, 2008, 135-150.

Vimont et al., "Growth of Shiga-Toxin producing *Escherichia coli* (STEC) and bovine feces background microflora in various enrichment protocols," Veterinary Microbiology, 123, 2007, 274-281.

Lermo et al., "Towards Q-PCR of pathogenic bacteria with improved electrochemical double-tagged genosensing detection," Biosensors and Bioelectronics, 23, 2008, 1805-1811.

Le et al., "Effect of the size of electrode on electrochemical properties of ferrocene-functionalized polypyrrole towards DNA sensing," Talanta, 81, 2010, 1250-1257.

Korri-Youssoufi et al., "Electrochemical biosensing of DNA hybridization by ferrocenyl groups functionalized polypyrrole," Analytica Chimica Acta, 469, 2002, 85-92.

Kim et al., "Application of a flow type antibody sensor to the detection of *E coli* in various foods," Biosensors and Bioelectronics, 18, 2003, 1101-1107.

Alfonta et al., "Chronopotentiometry and Faradaic irnpedance spectroscopy as signal transduction methods for the piocatalytic precipitation of an insoluble product on electrode supports: routes for enzyme sensors, irnrnunosensors and DNA sensors," Biosensors and Bioelectronics, 16.9, 2001, 675-687.

English language copy of the Written Opinion for PCT/FR2011/051624.

English language copy of the International Search Report for PCT/FR2011/051624.

May 29, 2015 Office Action issued in U.S. Appl. No. 13/808,485.

Jan. 23, 2017 Office Action issued in U.S. Appl. No. 13/808,485.

Dec. 1, 2017 Office Action issued in U.S. Appl. No. 13/808,485.

Oct. 5, 2018 Office Action issued in U.S. Appl. No. 13/808,485.

Oct. 1, 2019 Office Action issued in U.S. Appl. No. 13/808,485.

Jun. 10, 2020 Office Action issued in U.S. Appl. No. 13/808,485.

* cited by examiner

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Coding monomer

<400> SEQUENCE: 1
tttttttttt gaatcctcag tttttcaacg                                    30

<210> SEQ ID NO 2
<211> LENGTH: 20
<212> TYPE: DNA
<213> ORGANISM: Artificial Sequence
<220> FEATURE:
<223> OTHER INFORMATION: COMPLEMENTARY MONOMER

<400> SEQUENCE: 2
cgttgaaaaa ctgaggattc                                              20

PROCESS OF DIRECTLY DETECTING AND IDENTIFYING A MICROORGANISM IN A BIOLOGICAL SAMPLE DILUTED IN AN ENRICHMENT BROTH

CROSS-REFERENCE TO RELATED APPLICATIONS

This is a Continuation of application Ser. No. 13/808,485 filed Jan. 4, 2013, which issued as U.S. Pat. No. 10,907,190 on Feb. 2, 2021, which is a National Phase of International Application No. PCT/FR2011/051624 filed Jul. 7, 2011, which claims the benefit of French Application No. 1055574, filed Jul. 8, 2010. The disclosures of the prior applications are hereby incorporated by reference herein in their entireties.

REFERENCE TO AN ELECTRONIC SEQUENCE LISTING

The present application contains a Sequence Listing that has been submitted electronically and is hereby incorporated by reference in its entirety. The electronic Sequence Listing is named Sequence_Listing_ST25.txt, was created on Feb. 23, 2026, and is 819 bytes in size.

The present invention generally relates to the field of analysis for example biological analysis. More specifically, the present invention relates to a process of direct and real-time detection of a microorganism in a sample diluted or in suspension in an enrichment broth, inside a closed container.

Microbiological analysis requires precise techniques for which the time to obtain the result must be as short as possible.

In the medical field, it is necessary to envisage and diagnose the risk of infection: the faster and more precise the diagnosis, the more efficient the handling of patients and the more minimal the risk of transmission. The approach is similar for animal health.

In the agri-food field, the issues are identical. However, it singles out:
  the pathogenic microorganisms and their toxins whose presence is sought in raw materials, intermediate products, and marketed finished products,
  the non-pathogenic microorganisms used as quality indicators in the production process, from the raw materials to the finished products, along the whole chain, and
  bacteria of technological interest such as enzymes.

The rapid and precise detection of suspected contaminations allows them to be monitored and thus allows corrective actions to be taken.

Technically, the microbiological analysis may implement one or more pre-enrichment and/or enrichment phases, one or more detection phases, and one or more microorganism counting phases. For particular applications such as agri-food microbiological monitoring, a confirmation phase may also be required, in order to meet the standards in force in this field.

There is currently no method for detecting a target microorganism in a large initial sample quantity, without making use of an enrichment step.

The pre-enrichment and/or enrichment phase makes use of selective or non-selective culture media which aim to promote the growth of the target microorganisms in biological or environmental samples, whilst limiting the growth of the non-target flora. The media are often used in sterile plastic bag-type containers, in which they are placed in contact with food or environmental samples in order to re-suspend and re-enrich the microorganisms sought. This phase is necessary in order to meet the requirement of revealing the potential initial presence of at least one target microorganism in a very variable and possibly very large quantity of sample, e.g. 25 grams (g) to 375 g diluted in 225 to 3375 millilitres (mL) in the culture medium. At the end of this enrichment step, an aliquot (from 5 microlitres ($\mu$l) to 5 mL) is sampled to implement the step of detecting the target microorganisms. It is necessary to have a sufficient quantity of target microorganisms in this aliquot to allow their systematic detection.

The detection phase is historically based on culturing the microorganisms on agar media, to demonstrate the metabolic characters of the microorganisms sought. Specific enzymatic substrates are conventionally used. These enzymatic substrates are generally composed of two parts, a first part which is specific for the enzymatic activity which is to be revealed, also called the target part, and a second part acting as a marker, called the marker part, generally constituted by a chromophore or a fluorophore. By choosing these substrates depending on whether or not there is a reaction, it is possible to characterise the nature of a microorganism or differentiate between different groups of microorganisms. Thus the appearance or disappearance of a colouring or of a fluorescence will indicate a genus or a type of microorganisms. In this regard, the use of chromogenic media makes it possible to simultaneously detect and identify the germs sought. It simplifies the process and substantially reduces the time to obtain the result. By way of example, we would cite the applicant's ChromID® media. These chromogenic media are based on the detection of specific metabolic characters of the germs sought, such as beta-glucuronidase enzymatic activity for *Escherichia coli* for example.

Immunoassays constitute another of the technologies used for the detection test. They make use of the immunogenic characteristics of the microorganisms sought. Without being exhaustive, the competitive or sandwich-type ELISA (Enzyme Linked Immuno Sorbent Assay) techniques can be cited.

Finally, the molecular biology techniques based on the genomic characters of the microorganisms sought are also employed to detect and identify the target microorganisms. By way of example, it is possible to cite conventional amplification techniques such as PCR (Polymerase Chain Reaction) and the NASBA (Nucleic Acid Sequence Based Amplification), which can be coupled with real-time detection techniques known to the person skilled in the art.

However, the use of all of these techniques requires the bag to be opened at the end of the pre-enrichment/enrichment phase in order to recover an aliquot of the homogenate and to carry out the detection step.

The confirmation phase, for its part, is more particularly associated with the microbiological analysis in the agri-food field. Indeed, when the result of the methods set out above is positive, it is necessary to confirm the presence of the pathogen sought. This necessitates a complementary test and the use of a detection principle which is different to that used during the first analysis. The techniques described supra are used at will for the confirmation.

The complete and precise identification of a microorganism in a sample therefore necessitates a sequence of several steps: enrichment, detection and confirmation. The standardisation of the tests routinely used has permitted the automation of the detection methods, though their implementation remains long. Indeed, a disadvantage of the state of the art is that these steps are carried out sequentially and require a large number of time-consuming manipulations, thus impacting on the time necessary to yield results.

Furthermore, the techniques described supra require the enrichment bags to be opened once or more to sample the aliquots. The greater the number of negative samples during screening (particularly in agri-food industries), the more detrimental this is. It is therefore beneficial for the handler not to have to re-open the containers to find out the positivity/negativity result of the sample under consideration.

With regard to the technical problems associated with the state of the art considered above, one of the essential objectives of the present invention is to provide a simplified process for the detection, the identification and the confirmation of the microorganisms present in samples, in particular agri-food samples.

Another objective of the present invention is to provide a process for the detection, the identification and the confirmation of the microorganisms, which limits the handling of the sample contained in the container, thereby limiting the risks of contamination, both of the staff handling the sample and the sample itself.

Another objective of the present invention is to provide a process for the detection and the identification of microorganisms, which reduces the time necessary for the analysis of the sample.

Another objective of the present invention is to provide a process for the detection, the identification and the confirmation of the microorganisms on the total volume of the sample throughout the enrichment, manifestly increasing the measurement sensitivity, and even its specificity.

Another objective of the present invention is to provide a process which makes it possible to considerably increase the rate of sample analysis.

Another objective of the present invention is to provide a process which allows multi-detection.

Another objective of the present invention is to improve the traceability of the analysis by drastically reducing the sample handling steps.

These objectives amongst others are solved by the present invention, which firstly relates to a process of detecting at least one microorganism present in a sample placed in a closed container, said method comprising essentially the following steps:

a) Place said sample in contact in the container with at least one culture medium and a support capable of capturing the microorganism(s) to be detected, b) Close the container, c) Place the container under conditions capable of allowing the growth of the microorganism(s), d) Detect, inside said closed container, using detection means, the presence of the microorganism(s) fixed onto the capture support.

According to a particular embodiment, a revealing system capable of allowing the detection of the presence of the microorganism(s) is placed in contact in the container during step a).

Revealing system is understood to be any molecule capable of coupling with the microorganisms or the binding partners of said microorganisms which, by virtue of their transduction properties (fluorescence, colouring, radioactivity in particular), make it possible to reveal the presence of said microorganisms.

According to another particular embodiment, the process according to the invention includes an intermediate step c') consisting in transferring all or part of the mixture constituted by said sample, the culture medium, the support capable of capturing the microorganism(s) to be detected and potentially a revealing system, from the container, called in this case the main container, to at least one second container, called the secondary container, wherein it is possible to potentially perform a secondary enrichment by adding the nutritional elements and selective agents ad hoc into said secondary container beforehand. Such a secondary enrichment increases the population of the target microorganism(s) relative to that of the non-target microorganisms, which improves the specificity.

Advantageously, at least one specific or non-specific binding partner of the microorganism(s) is fixed onto the capture support. According to a preferred embodiment of the invention, the specific binding partner is taken from the group comprising: antibodies, Fab fragments, Fab' fragments, recombinant or non-recombinant phage proteins and phages or any other ligand well known to the person skilled in the art.

Advantageously, the detection means is taken from the group comprising: electrical detection means, in particular electrochemical detection means, optical detection means, acoustic detection means, thermal detection means, mechanical detection means and magnetic detection means.

The capture support may be a conventional support. In particular we shall cite particulate, potentially magnetic, supports or one-piece supports. It may simply be an inert support, such as a plastic or fibreglass plate. Such a capture support is then connected to the detection means. The capture support may be advantageously sensitised with a binding partner, potentially specific.

Alternatively, the capture support may be integral with the detection means. This is the case, for example, when the capture support is constituted by an electrochemical biosensor or an optical fibre.

According to a particular embodiment, it is entirely possible to envisage combining the detection means in order both to perform detection and to carry out confirmation simultaneously or subsequently. For example, it is possible to perform the detection of the target microorganism(s) by means of an electrochemical biosensor. If the target microorganisms are fixed via specific binding partners, the detection step in that case constitutes an identification step. An optical analysis of the microorganisms fixed specifically onto the biosensor at the analysis area by the optical detection device allows the identification of the microorganisms to be confirmed. If the optical detection device is a Raman spectrometer, an analysis of the Raman spectrum through comparison with a database of reference spectra corresponding to the different target microorganisms, then makes it possible to confirm the identification of said microorganism.

According to another particular embodiment, it is possible to perform the detection and the confirmation with the same technology. Thus, if the detection means is an optical means such as an intrinsic fluorescence measurement means, it is particularly advantageous to perform detection of the target microorganisms via the appearance of intrinsic fluorescence. The response is in that case yes (presence of fluorescence) or no (absence of fluorescence). If there is fluorescence, then a spectral analysis of the fluorescence signal compared to a database of reference spectra corresponding to the different target microorganisms allows said microorganism to be identified, and thereby allows the detection of the presence of said microorganism to be confirmed.

Preferably, the detection of the microorganism(s) is performed in real-time. Nevertheless, alternatively, the detection of the microorganism(s) may be accomplished, at the end, after the growth step of said microorganism(s).

According to a particular embodiment of the process according to the invention, the container is a homogenisation bag. Rigid containers such as flasks, bottles or pillboxes could equally well be used.

According to another particular embodiment of the process according to the invention, the detection means is connected to a data analysis system.

Advantageously, the connection between the detection means and the data analysis device is a wired connection or a wireless connection.

The invention also relates to an electrochemical biosensor for the detection of at least one microorganism present in a sample placed in a closed container. Said biosensor comprises a support including:

at least one detection electrode, coated with at least one electroactive polymer, onto one terminus of which is fixed at least one single-strand or double-strand oligonucleotide, the second terminus of said oligonucleotide being bound to at least one binding partner of the microorganism(s) to be detected, specific or non-specific;

at least one counter-electrode.

Advantageously, the electroactive polymer is taken from the group comprising polypyrrole, polyacetylene, polyazine, poly(p-phenylene), poly(p-phenylene vinylene), polypyrene, polythiophene, polyfuran, polyselenophene, polypyridazine, polycarbazole, and polyalinine.

According to a particular embodiment, the electroactive polymer includes at least one electrochemical mediator. Such an electrochemical mediator is taken from the group comprising ferrocene, quinone and derivatives of these or any other mediator well known to the person skilled in the art.

According to an alternative embodiment, the electrochemical mediator is in a free form in the culture medium. Such a mediator may be for example the ferricyanide/ferrocyanide pair $[Fe(CN)_6 3^-/4^-]$", the iridium chloride pair $[IrCl_6]3^-/4^-]$", or ruthenium hexamine $[Ru(NH_3)_6]3^+/2^+$.

The bond between the oligonucleotide and the binding partner of the microorganism(s) is preferably made by means of at least one biotin-streptavidin or biotin-avidin binding pair.

If the oligonucleotide is single-strand, a biotin is fixed onto the 3' terminus of said nucleotide, the 5' terminus allowing the latter to be bound onto the electroactive polymer, particularly by a covalent bond. By using a binding partner which is also biotinylated, it is then easy to bind this to the 3' terminus of the oligonucleotide via a molecule of streptavidin or avidin.

If the oligonucleotide is double-strand, the first strand is fixed, notably by a covalent bond, to the electroactive polymer via its 5' terminus. The second strand for its part is biotinylated at its 5' terminus, which allows the binding partner, also biotinylated, to be fixed via a streptavidin or avidin molecule.

Advantageously, the binding partner is taken from the group comprising: antibodies, Fab fragments, Fab' fragments, recombinant or non-recombinant phage proteins, and phages.

The aims and advantages of the present invention will be better understood in light of the following detailed description and the associated drawings in which.

Figure 1:
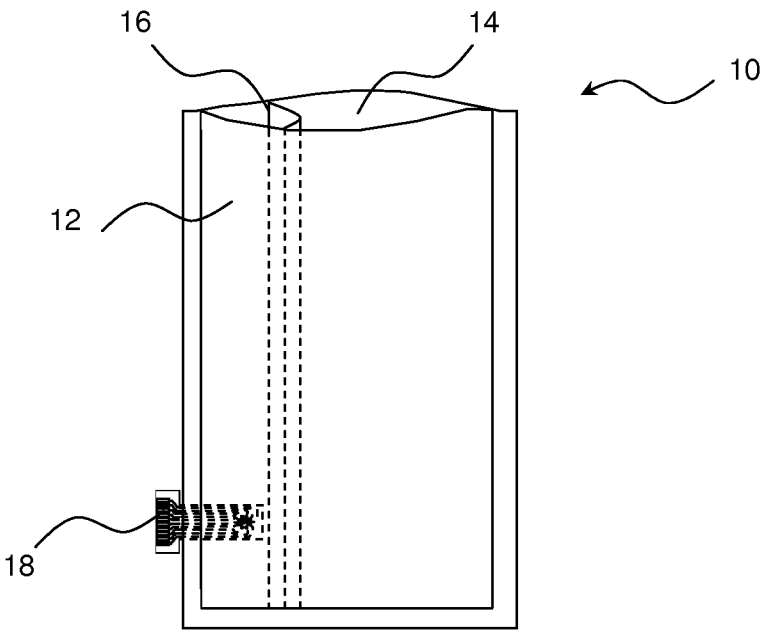
FIG. 1 depicts a pre-enrichment and/or enrichment bag in combination with an electrochemical biosensor.

According to a first embodiment of the present invention, the process of microorganism detection or identification consists in employing a sterile plastic homogenisation bag, conventionally called a Stomacher® bag. Such a bag is assigned the reference number 10 in FIG. 1. This bag 10 is constituted of two roughly rectangular plastic sheets, 12 and 14, joined to one another by 3 of their sides, so as to define an inner space for receiving the culture medium and the sample to be analysed. Its accessories comprise a roughly rectangular filter 16 connected to sheets 12 and 14 by one side, separating the inner space in two. The bag finally contains a biosensor 18. This biosensor is an electrochemical biosensor, depicted in detail in FIG. 2. The biosensor 18 is sandwiched between sheets 12 and 14, such that one part 181 corresponding to the detection area is found in the inner space of the bag 10, whereas a part corresponding to the connection area is outside the bag, so as to allow the chip to connect to a data analysis device. This is explained infra.

Figure 2:
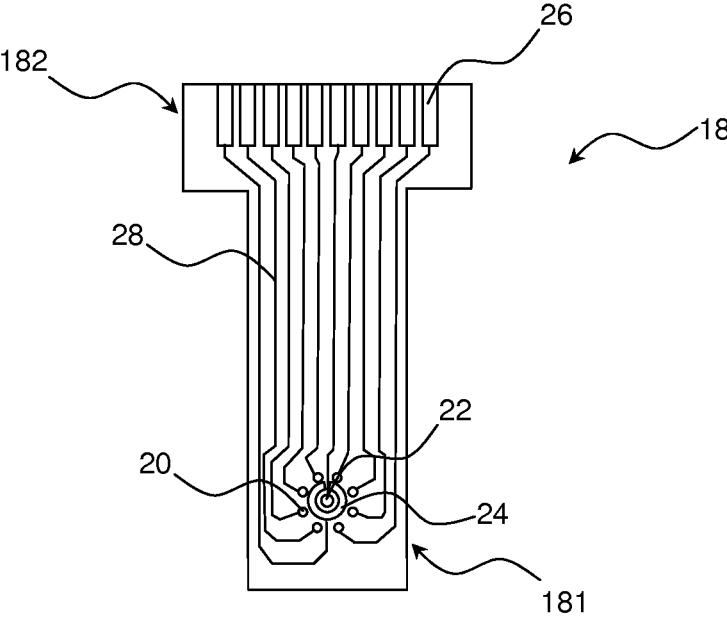
FIG. 2 depicts a front view of the electrochemical biosensor.

FIG. 2 depicts the electrochemical biosensor 18 in detail. As explained above, the biosensor 18 is constituted of an analysis area 181 and a connection area 182. The analysis area includes eight working electrodes 20, arranged around a central electrode, called the counter-electrode, 22. Furthermore, the analysis area contains a reference electrode 24, in the form of an open ring positioned around the counter-electrode 22. All of these electrodes are independently linked to ten connection terminals 26, by means of conductor tracks 28. The connection terminals are made of the same material as the working electrodes. This material is preferably gold. Nevertheless any other conducting material well known to the person skilled in the art may be used, such as carbon, platinum or diamond. The material constituting the support of the electrodes is a polymer material, such as polyimide. However it may be envisaged to use any other material with equivalent properties well known to the person skilled in the art.

It should be noted that the configuration of electrodes presented in FIG. 2 is only one configuration amongst others, and by no means limits the scope of the protection conferred by the present patent application.

Figure 3A:
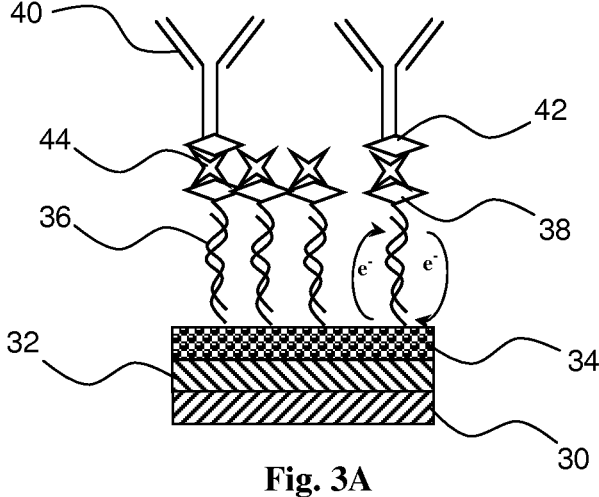
FIG. 3A is a depiction of the surface of the electrochemical sensor without the microorganism present.
Figure 3B:
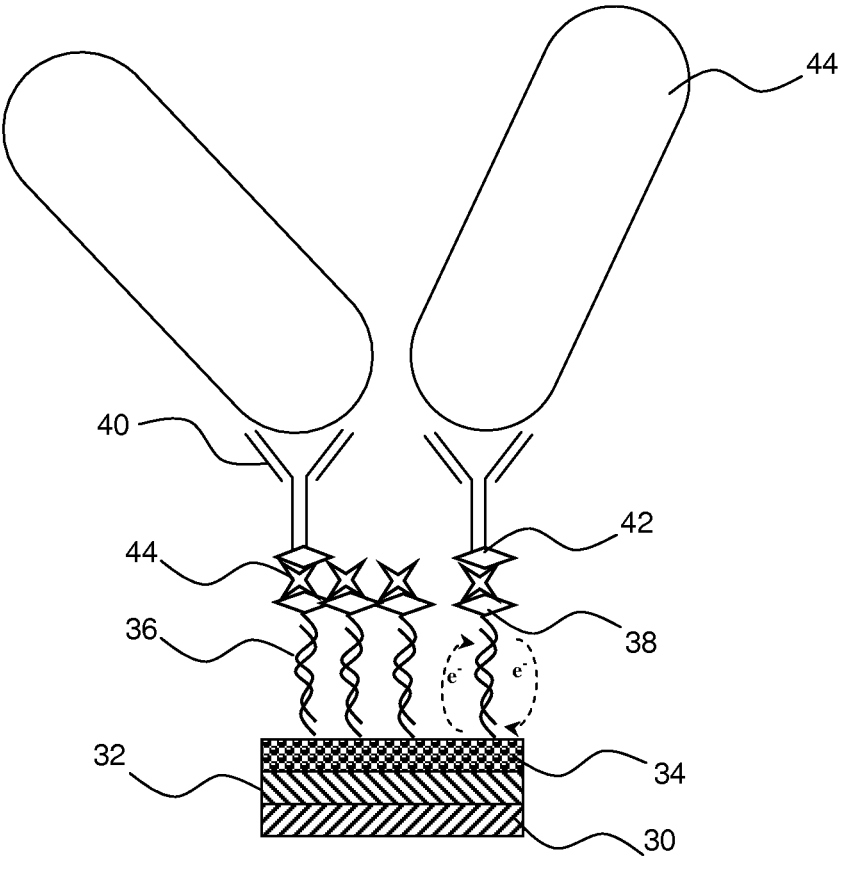
FIG. 3B is a depiction of the surface of the electrochemical sensor with the microorganism present.

FIGS. 3A and 3B depict a cross-section of a working electrode at microscopic level, in the absence or presence of microorganisms respectively.

At the working electrodes, three overlaid layers can be seen. The first of these layers 30 is the polymer layer constituting the biosensor support. The intermediate layer 32 is the layer of conductive material, typically gold. Finally, the layer 34 is a layer of electroactive conjugated polymer. Such a polymer is for example a polypyrrole. Such polymers are well known for their conductive and electroactive character. It is also known that polypyrroles maintain their conductivity and their electroactivity when certain pyrrole cycles are substituted in position 3 or 4 with functional groups. Polymers bearing this type of functional group are described in WO-A1-95/29199, Garnier et al. (Synthetic Metals, 100:89-94,1999) Ho-Hoang et al. (Synthetic Metals, 62:277-280, 1994), Ho-Hoang et al. (J. Mater. Chem., 6 (7), 1107-1112,1996), and Korri-Youssoufi et al. (Materials Science and Engineering, CI 5, 265-268,2001). Different molecules can thus be grafted onto the functional groups borne by a polypyrrole monomer. WO-A1-95/29199 thus describes the synthesis of a polypyrrole obtained by electro-oxidation at a potential greater than or equal to 0.8V/ECS. The synthesis of polypyrrole by electrochemical oxidation leads to the formation of an electroactive film at the surface of the electrode, more precisely on a conductive substrate in the form of a self-supported film. This is a method of indirectly immobilising oligonucleotides in polypyrrole. The pyrrole monomers substituted in position 3 of the pyrrole nucleus with functional groups are diluted in a solution of non-substituted monomers, which will immobilise the functional groups during their electrocopolymerisation by inclusion in the chain of functional units. In a second step, an anti-ligand such as an oligonucleotide, a polynucleotide or a peptide is chemically coupled onto the functional groups of the precursor polymer. The polymer thus obtained maintains its conductive and electroactive properties. These polymers can therefore be used to detect an analyte interacting specifically with the anti-ligand grafted onto the polymer by measuring a difference of potential or a variation in current: WO-A1-00/77523 also describes the chemical coupling of an anti-ligand, such as an oligonucleotide, onto a precursor polymer bearing functional groups.

This can also be a method of directly immobilising oligonucleotides in polypyrrole by electrocopolymerisation. The pyrrole monomers substituted in position 3 of the pyrrole nucleus with oligonucleotides are diluted in a solution of non-substituted monomers, which will immobilise the oligonucleotides directly during their electrocopolymerisation by inclusion in the chain of functional units.

Onto this layer of electroactive polymer, there is grafted a double strand of nucleic acid 36, via the 5' terminus of one of these strands, with the complementary strand bearing a biotin molecule 38 at its 5' terminus, so that a bond to a specific binding partner also bound to a biotin 42 is possible via a streptavidin molecule 44. The specific binding partner 40 depicted in FIGS. 3A and 3B is an antibody. It can be either one or more monoclonal or polyclonal antibodies. It may also be an antibody fragment, such as a Fab or Fab'2 fragment, as well as any antibody obtained by genetic modification or recombination and specific of a particular microorganism.

Alternatively, the specific binding partner may be a phage or a recombinant phage protein, which binds specifically to the target microorganisms. Such proteins and their use for the capture of bacteria were described in patent EP-B-1 356 080 amongst others.

It should be noted that the structure depicted in FIGS. 3A and 3B is only one example amongst others and is by no means to be understood as a restriction of the invention. In fact, as a variation, it can be envisaged to fix the anti-ligand molecule directly onto the electrode without using the double strand of nucleic acid.

In order to perform analysis, the electrochemical biosensor, joined to the homogenisation bag, is placed in contact with the dispersed sample, the culture medium and an electrochemical mediator, such as the ferricyanide-ferrocyanide pair. In the absence of microorganisms, an electron exchange takes place between the electroactive conjugated polymer and said redox system present in the reaction medium. This is shown in FIG. 3A. The electron exchange is transformed into electric current and measured by electrochemical spectroscopy, using a potentiostat, as explained infra.

When the sample contains microorganisms 44, these are captured by the anti-ligand molecules 40. The presence of microorganisms in the vicinity of the electrode brings about a steric hindrance, which disrupts and diminishes the electron flow between the electrode modified by the electroactive conjugated polymer and said redox system present in the reaction medium. This modification is then measured by impedance measurement and characterised by the load transfer resistance, a resistance of which the value increases when the bacteria is captured (positive result).

Figure 4:
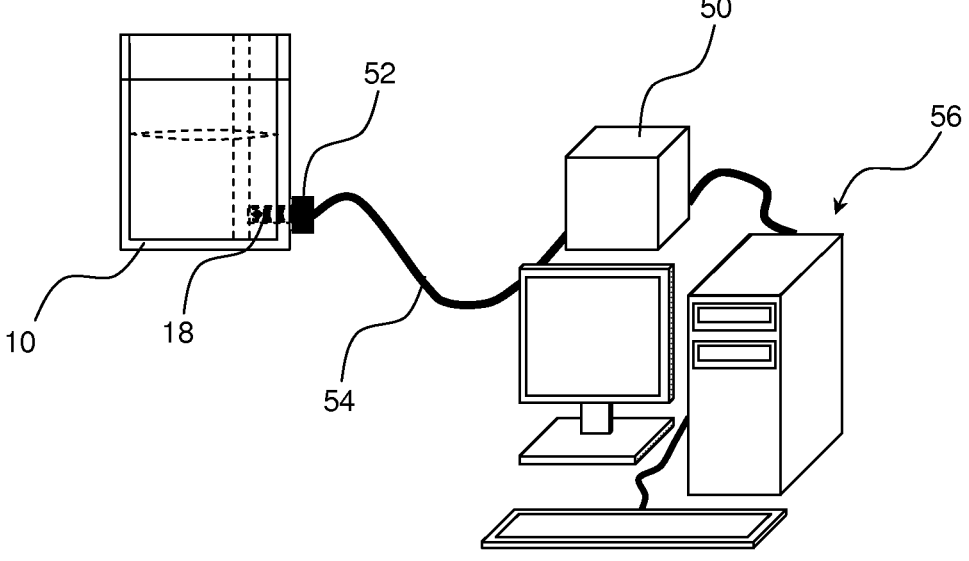
FIG. 4 is a schematic depiction of a system for analysing the pre-enrichment/enrichment bag with the electrochemical biosensor.

The analysis results measurement system is depicted schematically in FIG. 4, according to a first embodiment. As can be seen in this figure, the bag 10, by means of its biosensor 18, is connected to a potentiostat 50. This connection is made via a connector 52, which is connected to the connection area 182 of the biosensor 18. The connector 52 is extended by a cable 54 linked to the potentiostat 50. The potentiostat is, for its part, linked to a computer system 56 capable of recording and analysing the impedance measurement data.

For the purposes of detection of the microorganisms, the homogenisation bag 10 is preferably incubated for as long as needed to allow the microorganisms to grow. This incubation may be conventionally performed in an incubator at a temperature of between and 45° C. The incubation time may vary from 3 to 72 hours depending on the initial quantity of microorganisms present in the sample and on the type of microorganism to be detected.

According to a first embodiment, the impedance measurement may be performed at the end. In fact, the homogenisation bag is incubated for the time deemed necessary and sufficient for the growth of the microorganisms, then it is removed from the incubator and connected to the impedance measurement system described supra. The impedance measurement is then performed and the result is compared to a reference impedance value. Such an impedance measurement is possible insofar as one or more working electrodes 20 are coated with electroactive conjugated polymer and/or a non-specific anti-ligand molecule for the microorganism to be detected. The impedance measurement at this/these electrode(s) constitutes the reference impedance value. Insofar as the difference between the impedance value on the detection electrodes (electrodes onto which the anti-ligand molecules of the target microorganism are directly or indirectly fixed) and the reference value is greater than a threshold value, the detection of the microorganisms is effective.

According to a second embodiment, dotted, namely by spot impedance measurements during the incubation. In this case, the homogenisation bag is removed from the incubator and connected to the impedance measurement system, for the time needed for measurement, and is then incubated again. The interval between two measurements may be between 30 seconds to 2 minutes. This second embodiment has as its main advantage over the first embodiment the ability to detect the presence of the microorganisms after a shorter incubation time.

Finally in a third embodiment which is the preferred embodiment, it is envisaged to have inside the incubator a means for connecting the biosensor to the impedance measurement system. It may be a wired or wireless connection system. Such an embodiment is particularly advantageous because it makes it possible to carry out a measurement at regular intervals inside homogenisation bags without having to handle the latter. Furthermore, the impedance measurement at regular intervals makes it possible to carry out detection of microorganisms in real time. When linked to a computer system alerting technical personnel when a detection is made, the latter are no longer constrained by the workflow consisting of performing measurements successively over time. Their intervention is only required when a microorganism is detected in a bag.

A wired connection means is constituted by any means which makes it possible to connect two electronic devices to each other in order to enable data transmission. In particular, a wired connection means may be a serial connection system (RS 485, RS 232 standard), USB connection system (Universal Serial Bus), network connection system (Ethernet), parallel connection system (GPIB) or any other equivalent means.

A wireless connection means is a radio wave transmitter-receiver. For example, it may be a Wi-Fi (802.11b standard), Bluetooth (802.15 standard) or ZigBee (802.15.4 standard) system.

According to an alternative, the data acquisition means may be a RFID (Radio Frequency Identification) reader, a Labjack card or any other means well known to the person skilled in the art.

According to an alternative to the process according to the invention, this may be implemented via an optical detection means. This detection means may be independent of the capture support. This is the case for example with an optical sensor, such as a camera. Alternatively, the optical detection means and the capture support may be integral. This is the case for example with an optical fibre, the end of which acts as a capture support.

Figure 7:
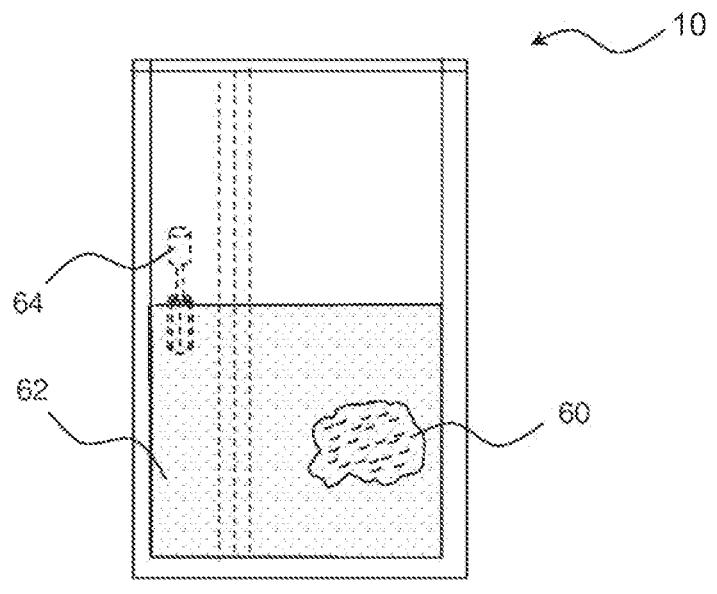
FIG. 7 is a schematic depiction of an analysis system by optical detection in a pre-enrichment/enrichment bag with a sensitised capture support, according to a first embodiment.

Such an alternative is depicted in FIG. 7. A closed homogenisation bag 10, as described previously, is incubated with a food sample 60, constituted here by a sample of minced steak. This food sample 60 is plunged into a culture medium 62, implemented with a revealing system. A sensitised capture support 64, held in place in the bag by any appropriate means, is also placed into the homogenisation bag 10 and is immersed in the culture medium 62. The sensitised capture support 64 is functionalised by at least one binding partner specific to a target microorganism to be detected. The capture support may be constituted of any support capable of fixing the specific binding partners and well known to the person skilled in the art. By way of non-limiting example, an appropriate capture support may be made of irradiated polystyrene, such as that marketed by the company Nunc/Thermo Scientific (Cat. No. 472230). Such a capture support is depicted schematically in FIG. 9, under the reference 64. Advantageously and according to a preferred embodiment, the lower part may be divided in two. The zone bearing the reference 641 may be sensitised with a solution of binding partners (polyclonal antibodies, monoclonal antibodies, Fab' or Fab'2 fragments, phage proteins), whereas the upper part 642 remains free from any binding partner and thus acts as a negative control.

The capture support is functionalised by at least one specific binding partner such as antibodies, aptamers, phages, recombinant phage proteins, or any equivalent means enabling the specific capture of the target bacteria.

These latter may be coloured simultaneously with their growth thanks to the revealing system contained in the culture medium.

According to a particular example, the revealing system is based on TTC reduction by the microorganisms. Simultaneously to the growth, the TTC (colourless in its non-reduced form) is internalised by said microorganisms, then reduced by the latter into triphenyl-formazan (red), thus colouring said microorganisms red and allowing them to be revealed on the support.

The process of direct real-time detection of microorganisms in a food sample, during the incubation period, is carried out automatically or non-automatically by the optical reading of a sensitised capture support. The incubation may be performed at temperatures between 25 and 44° C. for 6 to 48 h.

In addition, once a certain quantity of coloured dyed microorganisms (in the case of a positive sample) is effectively captured, a change to the optical properties of the support takes place by the appearance of a red colouring thereon (i.e. transduction of the biological signal). This colouring of the capture support is then detectable to the eye or measurable via the use of a reading machine such as a camera. The capture support is depicted schematically in FIG. 10 after analysis giving a positive result. As can be seen, area 641 appears coloured due to the fixing of the target microorganisms on the specific binding partners. The area 642, acting as the negative control, remains the starting colour of the capture support.

Figure 8:
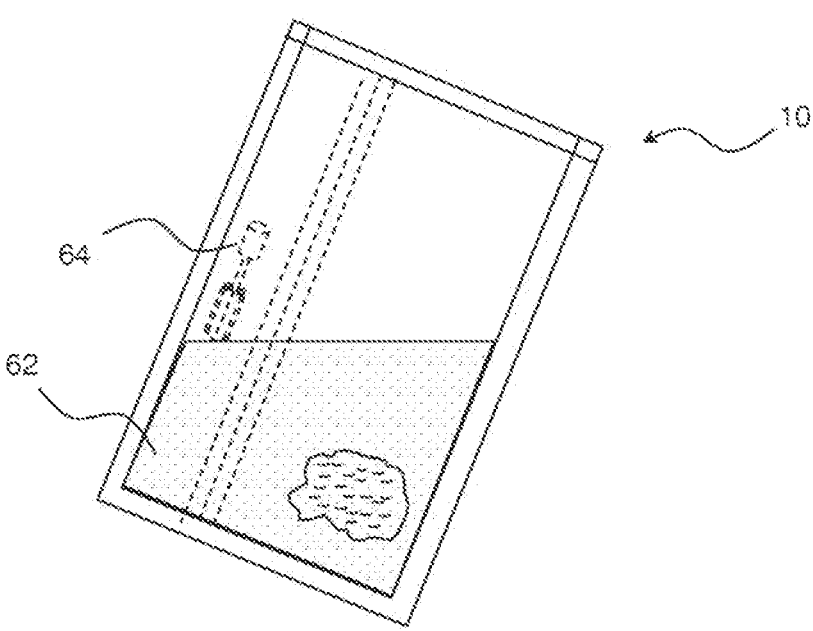
FIG. 8 is a schematic depiction of the analysis system as depicted in FIG. 7, in a bag position which allows the sensitised capture support to be read.

To facilitate reading, it is preferable for the sensitised capture support to no longer be in contact with the culture medium. To this end, it may be envisaged, for example, to tilt the homogenisation bag 10, which is well depicted in FIG. 8. As explained supra, the reading may be carried out at the end on a spot basis, or in real-time.

According to another alternative of the process according to the invention, the capture support is constituted by sensitised particles, namely bearing a specific or non-specific binding partner for the microorganism(s) to be detected. The detection is then preferably demonstrated by the appearance of real-time agglutination of the sensitised particles, via the target microorganisms bound to the latter, during the incubation period. Such an embodiment is described in document WO-A-2009/122069.

According to a particular embodiment, the sensitised particles may be magnetic particles. This embodiment consists in directly detecting, via the agglutination of sensitised magnetic particles, the presence of the target microorganism (i. e. E. coli O157: H7) in a food sample during enrichment. The detection is performed during the incubation period by immersing the sensitised magnetic particles with a specific binding partner (i.e. anti-E. coli O157: H7 recombinant phage protein) in the closed container which contains the food sample, diluted in the culture medium.

Figure 11:
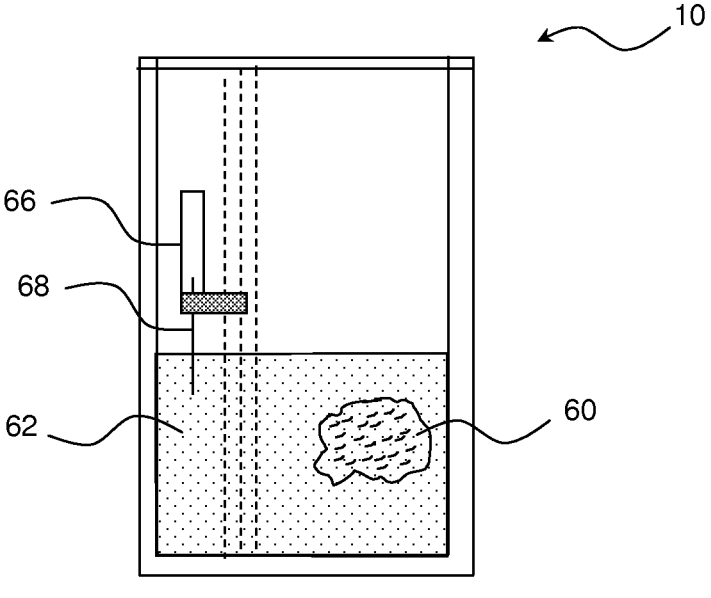
FIG. 11 is a schematic depiction of a system of analysis by optical detection in a pre-enrichment/enrichment bag with a sensitised capture support, according to a second embodiment.

In this alternative, it may be advantageous to use a secondary, tube-type container inside the main container (homogenisation bag) in order to improve the demonstration of the agglutination of sensitised particles. As can be seen from FIG. 11, the homogenisation bag 10 contains in addition to the culture medium 62 and sample 60, a tube 66. This tube 66 is in fluid communication with the culture medium 62 contained in the homogenisation bag 10 via a conduit 68. A fraction of the culture medium 62 containing the food sample may then be transferred into the tube 66, in which the detection takes place. Such a transfer may notably be achieved through temperature changes, based on the law of perfect gases (PV=nRT). Such a process is described in document WO-A-2004/092401.

In the case of use of magnetic particles, the reading in the secondary container containing the reaction medium at the end of the incubation period is carried out using a magnetic reader.

The magnetic signal can be amplified by prior use of a magnetic field (via a magnet) which concentrates the agglutination at the centre of the reading area.

The application of a magnetic field may also improve the detection limit when this phenomenon triggers the formation of an agglutination, following a coming together of the magnetic particles which have captured the microorganisms. In fact, if the microorganism concentration is not sufficient to trigger passive agglutination, the coming together of the magnetic particles, some of which will have previously captured the microorganisms, will force an agglutination. Furthermore, the repetition of this sequence (i.e. magnetisation and re-suspension) may also amplify the phenomenon of capturing and agglutination formation and thus amplify the sensitivity of the analysis.

The examples set out hereafter aim to present different embodiments of the process according to the invention and the results obtained. They by no means limit the invention.

EXAMPLES

Example 1: Preparation of the Analysis Electrodes of the Electrochemical Biosensor Reagents:

Lithium perchlorate ($LiClO_4$), sodium chloride (NaCl), sodium hydroxide (NaOH), potassium (III) hexacyanoferrate ($K_3Fe(CN)_6$), potassium hexacyanoferrate (II) trihydrate ($K_4Fe(CN)_6$; $3H_2O$), Tween 20, phosphate buffer (BPS), bovine serum albumin (BSA), tris(hydroxymethyl) aminomethane (TRIS), maleic acid, salmon DNA and 50×Denhardt come from Sigma-Aldrich.

The wash buffer, pH 7.2, is PBS 0.01M, NaCl 0.5M and 0.05% Tween.

The hybridisation buffer is PBS 0.01M, NaCl 0.5M, 2×Denhardt and salmon DNA at 10 g/mL.

The grafting buffer of the binding partner is the TRIS-MALEATE BSA buffer, pH 6.2, constituted of 24.23 g/L TRIS, 23.2 g/L maleic acid, 6 g/L sodium hydroxide and 5 g/L BSA.

3-(2-hydroxyethyl) pyrrole or PyOH and 3-(phthalimide ethanoate) pyrrole or PyNHP are supplied by EZUS Lyon.

Synthetic oligonucleotides containing 20 nucleotides and bearing an amino group at the 5' terminus are fixed covalently by substitution of the NHP groups. The functional monomer is as follows:

(SEQ ID NO: 1)
Pyr-5′TTTTTTTTTTGAATCCTCAGTTTTTCAACG3′.

The complementary nucleotide bears a biotin group at the 5' terminus. Its sequence is as follows:

(SEQ ID NO: 2)
5′CGTTGAAAAACTGAGGATTC3′.

Biosensor and Electrochemical Detection Equipment:

The electrochemical detection measurements are carried out using a computer-controlled BioLogic potentiostat from Sciences Instruments.

The sensor used is derived from printed circuit board (PCB) technology. The gold deposition on the electrodes is a galvanic deposition by electrolysis from a gold-based bath. The electrodes are composed of an epoxy resin, copper, nickel and gold multilayer.

Preparation of the Electrodes

To wash the electrodes, the analysis area of the sensors is soaked in a 1:1 distilled water/ethanol solution for one minute in an ultrasound bath.

After washing, the sensors are cleaned and activated electrochemically. To do this, one 30 μL drop of 0.2 M NaOH in distilled water is deposited on the analysis area of the sensor, so as to wet all of the electrodes. The sensor is connected to a potentiostat and several cycles of potential jump in oxidation and in reduction are generated by chronoamperometry. The aim of this step is to generate oxygen bubbles at the interface with the electrodes so as to eliminate any organic and/or inorganic contaminant. The sensor is then rinsed with distilled water.

The surface of the working electrodes is modified by copolymer electrodeposition. All of the electrodes are thus covered with a drop of electropolymerisation solution, 100 mM of PyOH and 25 μM of PyODN (1/4000 concentration ratio) and 0.5 M $LiCLO_4$. The reaction is then electroconducted by application of a fixed potential of 0.8V/gold pseudo reference, generated by chronoamperometry. The polymerisation is interrupted once the imposed charge of 11 $mC/cm^2$ is reached. The copolymer is formed simultaneously on all of the working electrodes. The electrodes are then rinsed with distilled water.

The following step consists in hybridisation. The sensor is covered with one 30 μL drop of buffer solution in the presence of 100 nM of biotinylated target ODN. The hybridisation is performed at 37° C. for 30 minutes. After a washing step with PBS buffer, the sensor is soaked in a 100 μg/mL streptavidin solution in PBS buffer for 15 minutes with agitation. The anti-ligand molecule is then fixed by placing the sensor in contact with a solution of 1 μg/mL anti-ligand molecule in the TRIS-maleate BSA buffer.

In the following examples, the anti-ligand molecule is either a recombinant phage protein for the detection of *E. coli o*157, or a Fab' fragment for the detection of *Listeria* spp.

Example 2: Detection of *E. coli* O157: H7 in a Food Sample

A biosensor functionalised with recombinant phage proteins specific to *E. coli* O157, such as described supra and joined to a homogenisation bag, is incubated with a food sample.

Two bags containing the biosensors are incubated with positive enrichment preparations. Two bags containing the biosensors are incubated with the negative enrichment preparations, and two bags containing the biosensors are incubated with an uncontaminated enrichment preparation in order to measure the background noise of the food matrix.

Positive enrichment preparation 25 g of raw meat having a minimum 5% of fatty material are placed aseptically into the Stomacher® R bag with a filter and placed in contact with *E. coli* O157: H7 ATCC 43888. The bag is placed for 24 hours at 2-8° C. to stress the strain.

225 mL of buffered peptone water (bioMérieux ref. 42043) preheated for 24 hours at 41.5° C. and 5 mM of redox probe [Fe(CN)$_6$]3$^{-}$/4$^{-}$" are then added to the sample.

The growth of the *E. coli* O157: H7 bacteria in the presence of 5 mM of redox probe [Fe(CN)$_6$]$^{3-/4-}$ was verified previously. It was confirmed that the presence of this redox probe did not slow down the bacterial growth within a culture medium.

After homogenisation of the suspension, a functionalised capture support is placed into the Stomacher®® bag.

This protocol is repeated in order to test two positive suspensions by means of two bags containing a functionalised support.

A count on a Petri dish, from two positive suspensions, made it possible to evaluate, before incubation in the Stomacher®® bag, an average concentration of *E. coli* O157: H7 ATCC 43888 of 0.92 CFU/g of raw meat.

The preparation is then incubated at 41.5° C. for 3 hours.

Preparation of the Negative Enrichments

Negative control: from the same raw meat batch number, 25 g are placed aseptically into a Stomacher®® bag with a filter and placed in contact with *Bacillus cereus* ATCC 27522. The bag is placed for 24 hours at 2-8° C. to stress the strain.

225 mL of buffered peptone water (bioMérieux ref. 42043) preheated for 24 hours at 41.5° C. and 5 mM of redox probe [Fe(CN)$_6$]$^{3-/4-}$ are then added to the sample.

After homogenisation of the suspension, a functionalised capture support is placed into the bag.

This protocol is repeated in order to test two negative suspensions by means of two bags containing a functionalised support.

In the two suspensions, the rates of contamination by *Bacillus cereus* ATCC 27522, before incubation in the Stomacher®® bag, are evaluated at 1.32 CFU/g of raw meat (theoretical measurement).

The preparation is then incubated at 41.5° C. for 3 hours.

Measurement of the background noise generated by the matrix: the same protocol is repeated without bacteria. The preparation is then incubated at 41.5° C. for 6 hours.

The aim of this test is to verify if it is possible to detect *E. coli* O157: H7 after 3 hours of incubation/enrichment. Results Obtained:

For each bag, the impedance measurement is performed directly, without the step of washing the biosensor.

Figure 5:
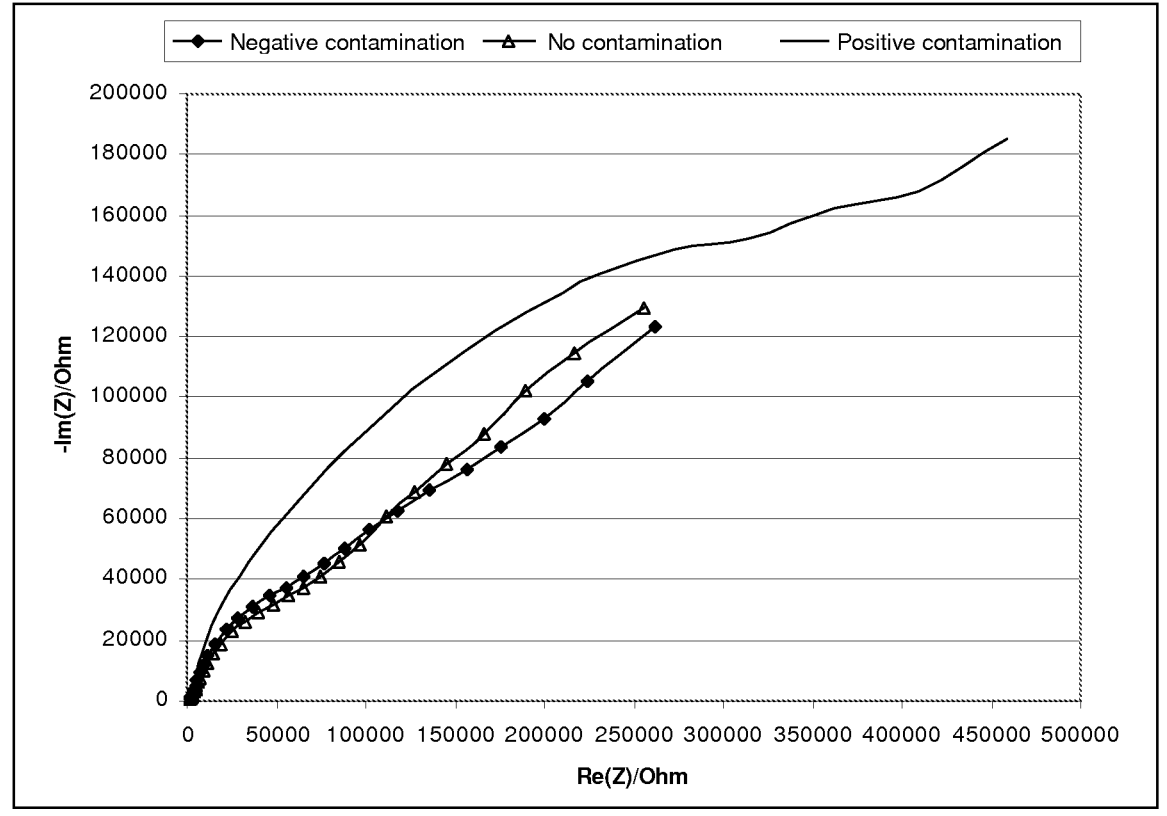
FIG. 5 is a graph of impedance spectrometry measurements obtained during the detection of *E. coli* O157:H7 in a food sample.

The Nyquist graphs (-Im(z) vs. Re(z)) obtained at 200 mV in a frequency scale of between 1 Hz to 100 kHz are set out in FIG. 5.

The electrochemical impedance spectrum obtained after 6 hours of incubation of the raw meat preparation in the Stomacher® bag without contamination, and that obtained after 3 hours of incubation of the raw meat preparation with negative contamination show the same electron transfer resistance R$_{ct}$ (diameter of the semicircles), the values are respectively equal to 116 and 115 kΩ.

The resistance to electron transfer is thus attributed to the background noise of the matrix, which is identical to the resistance to electron transfer during non-target bacteria growth.

After 3 hours of enrichment of the raw meat preparation with positive contamination, by *E. coli* O157: H7 (0.92 CFU/g of raw meat), the electron transfer resistance value is 719 kΩ, i.e. around six times greater than that obtained with the negative contamination and so allows clear detection of *E. coli* O157: H7.

The average R$_{ct}$ value obtained with all of the homogenisation bags, the standard deviation and variation coefficient values, are set out in table 1 below. The values indicated are the gross values of charge resistance corresponding to the diameter of the semicircle of the impedance signal.

TABLE 1

| | Matrix background noise (without contamination) | Negative contamination *B. cereus* (1.32 CFU/g) | Positive contamination *E. coli* (0.92 CFU/g) |
|---|---|---|---|
| Average R$_{ct}$ (kΩ) | 109 | 90 | 708 |
| Standard deviation | 9 | 8 | 25 |
| Variation coefficient (%) | 8 | 9 | 4 |
| Number of measurements | 16 | 7 | 16 |

Example 3: Detection of *Listeria innocua* in a Food Sample

A biosensor functionalised with Fab' fragments specific to *Listeria*, such as described supra and joined to a homogenisation bag is incubated with a food sample.

One bag containing the biosensors is incubated with a positive enrichment preparation. One bag containing the biosensors is incubated with a negative enrichment preparation.

Preparation of the Positive Enrichment 25 g of raw meat having a minimum 5% of fatty material are placed aseptically into a Stomacher® bag with a filter and placed in contact with *Listeria innocua* ATCC 33090. The bag is placed for 22 hours at 2-8° C. to stress the bacteria.

225 mL of *Listeria* Xpress broth (bioMérieux ref. 42626) preheated for 18 hours at 30° C. and 5 mM of redox probe [Fe(CN)$_6$]3$^{-}$/4$^{-}$" are then added to the sample.

The growth of the *Listeria innocua* bacteria in the presence of 5 mM of redox probe [Fe(CN)$_6$]3$^{-}$/4$^{-}$" was verified previously. It was thus confirmed that the presence of this redox probe did not inhibit bacterial growth within a culture medium.

After homogenisation of the suspension, two functionalised capture supports are placed into the Stomacher® bag.

A count on a Petri dish made it possible to evaluate the *Listeria innocua* ATCC 33090 concentration, before incubation in the Stomacher® bag, at 0.48 CFU/g of raw meat.

The preparation is then incubated at 30° C. for 6 hours.

Preparation of the Negative Enrichment

Negative control: from the same raw meat batch number, 25 g are placed aseptically into a Stomacher® bag with a filter and placed in contact with *Staphylococcus aureus* ATCC 6538P. The bag is placed for 22 hours at 2-8° C.

225 mL of *Listeria* Xpress broth (bioMérieux ref. 42626) preheated for 18 hours at 30° C. and 5 mM of redox probe $[Fe(CN)_6]3^-/4^-$'' are then added to the sample.

After homogenisation of the suspension, two capture supports are placed into the Stomacher® bag. The *Staphylococcus aureus* ATCC 6538P concentration is $4.10^7$ CFU/g of raw meat (theoretical measurement), before incubation in the Stomacher® bag.

The preparation is then incubated at 30° C. for 6 hours.

The aim of this test is to verify if it is possible to detect *Listeria* genus bacteria after 6 hours of incubation/enrichment.

Results Obtained:

For each bag, the impedance measurement is performed directly, without the step of washing the biosensor.

Figure 6:
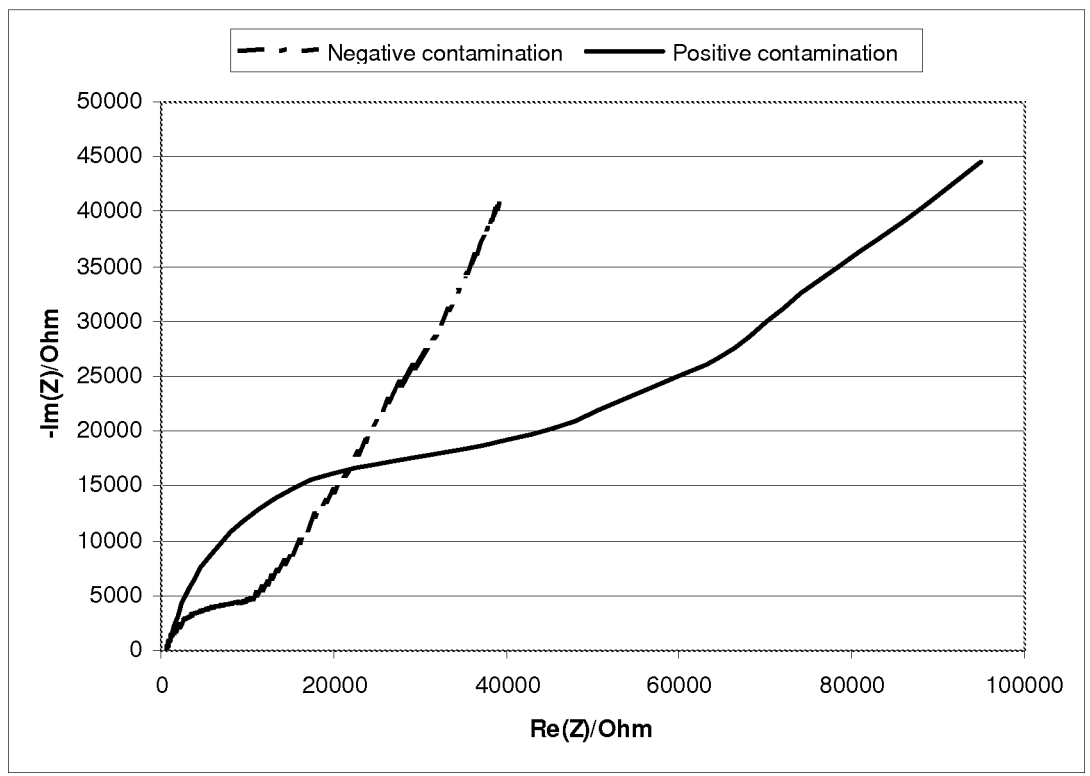
FIG. 6 is a graph of impedance spectrometry measurements obtained during the detection of *Listeria innocua* in a food sample.

The Nyquist graphs (-Im(z) vs. Re(z)) obtained at 200 mV in a frequency scale of between 1 Hz to 100 kHz are set out in FIG. 6.

The electrochemical impedance spectrum obtained after 6 hours of incubation of the raw meat preparation in the homogenisation bag with negative contamination (*Staphylococcus aureus* at $4.10^7$ CFU/g) (FIG. 6 broken line) shows an electron transfer resistance value is of 13 kΩ.

After 6 hours of enrichment of the raw meat preparation with positive contamination, by *Listeria innocua* ATCC 33090 (0.48 CFU/g of raw meat before incubation) (FIG. 6 unbroken line), the electron transfer resistance value is 45 kΩ, i.e. around three times greater than that obtained with the negative contamination. This result clearly shows that it is possible to detect the presence of *Listeria innocua* bacteria present in a food sample with the specific Fab' fragments fixed on an electrochemical biosensor in contact with an enrichment medium containing said sample without the step of washing the sensor, and without signal amplification.

The average $R_{ct}$ value obtained with all of the homogenisation bags, the standard deviation and variation coefficient values are set out in table 2 below. The values indicated are the gross charge resistance values corresponding to the diameter of the semicircle of the impedance signal.

TABLE 2

|  | Negative contamination *S. aureus* ($4.10^7$ CFU/g) | Positive contamination *L. innocua* (0.48 CFU/g) |
|---|---|---|
| Average $R_{ct}$ (kΩ) | 15 | 45 |
| Standard deviation | 1 | 8 |
| Variation coefficient (%) | 5 | 17 |
| Number of measurements | 16 | 12 |

Example 4: Elaboration of a Capture Support Sensitised with at Least One Binding Partner Specific to the Target Microorganism for Optical Detection A capture support, made of irradiated polystyrene, sold by the company Nunc/Thermo Scientific (Cat. No. 472230) and shown in FIGS. 9 and 10.

The sensitisation of the capture support is performed in six steps, as follows:

1) the polystyrene support is immersed at 37° C. for one night in a 5 μg/mL Biotinylated BSA (Bovine Serum Albumin) solution in carbonate buffer pH 9.6;

2) the support is then rinsed with a PBS buffer for several seconds;

3) after rinsing, the support is immersed at 37° C. for two hours in a 10 μg/mL streptavidin solution in phosphate buffer at pH 7.2;

4) the support is then rinsed with a carbonate buffer at pH 9.6 for several seconds;

5) the support is then immersed for two hours at 37° C. in a solution of specific binding partners (1 μg/mL to 40 μg/mL) in carbonate buffer at pH 9.6;

6) the support is finally passivated in a solution of BSA in carbonate buffer at pH 9.6, for two hours at 37° C.

The sensitised support thus elaborated may be used for optical detection of the microorganisms or kept at 2-8° C. for later use.

Example 5: Optical Detection of *Escherichia coli* O157: H7 in a Food Sample Via the Use of a Sensitised Support The aim of this experiment is to directly detect, via the use of a sensitised support such as described supra and shown in FIG. 8, the presence of the target bacteria *E. coli* O157: H7 in a food sample during enrichment.

As detailed hereafter, the detection is carried out during the incubation period by immersing the sensitised capture support with an anti-*E. coli* O157: H7 recombinant phage protein in a homogenisation bag containing the food sample, diluted to ⅒th in the reaction medium.

Protocol:

Step 1: Re-Suspension of the Samples in the Reaction Medium

Four samples are prepared as follows:

Sample A: in a homogenisation bag, 25 g of minced steak contaminated by 5 colony-forming units (CFU) of *E. coli* O157: H7 are re-suspended in 225 mL of BPW (bioMérieux, Ref. 42043) supplemented by 0.01 g/L of vancomycin (Sigma, Cat. No. 75423) and 0.3 g/L of TTC (bioMérieux, Ref. 04568088);

Sample B: in a homogenisation bag, 25 g of minced steak not contaminated by *E. coli* O157: H7 are re-suspended in 225 mL of BPW supplemented by 0.01 g/L of vancomycin and 0.3 g/L of TTC;

Sample C: in a homogenisation bag, 375 g of minced steak contaminated by 5 CFU of *E. coli* O157: H7 are re-suspended in 3375 mL of BPW supplemented by 0.01 g/L of vancomycin and 0.3 g/L of TTC;

Sample D: in a homogenisation bag, 375 g of minced steak not contaminated by *E. coli* O157: H7 are re-suspended in 3375 mL of BPW supplemented by 0.01 g/L of vancomycin and 0.3 g/L of TTC;

The analysis is carried out three times for each sample.

Step 2: Immersion of the Sensitised Supports in the Homogenisation Bags Before Incubation The sensitised capture support is placed in each stomacher bag (Samples. A, B, C and D), as described hereafter. The homogenisation bags are then reclosed by means of a closing pin and incubated in an incubator at 41.5° C. for 16-24 h.

Step 3: Reading the Capture Supports after the Incubation Period

At the end of incubation (20 h at 41.5° C.) and following the non-specific reduction of the TTC by all of the bacteria present in the sample (i.e. belonging to the annex flora and the target flora), the reaction medium is red in colour. Finally, in order to be able to observe the capture support which reveals the positivity or negativity of the analysed sample, the homogenisation bags are inclined in order to isolate said capture support from the reaction medium.

In accordance with the experimental plan, samples B and D are positive whereas samples A and C are negative. The analysis of these same samples by the VIDAS® ECPT method marketed by the applicant (ref. 30122) led to similar results, thus confirming the results obtained via optical reading of the sensitised capture support.

Finally, the target levels reached after 20 h of incubation are around 5.5 log 10 CFU/mL for sample B and 3.5 log$_{10}$ CFU/mL for sample D.

Example 6: Optical Detection of *Listeria* Spp in Environmental Samples Via the Use of a Sensitised Support The aim of this experiment is to directly detect, via the use of a sensitised support, the presence of the bacterial strains belonging to the genus *Listeria* in environmental samples during enrichment.

Figure 10:
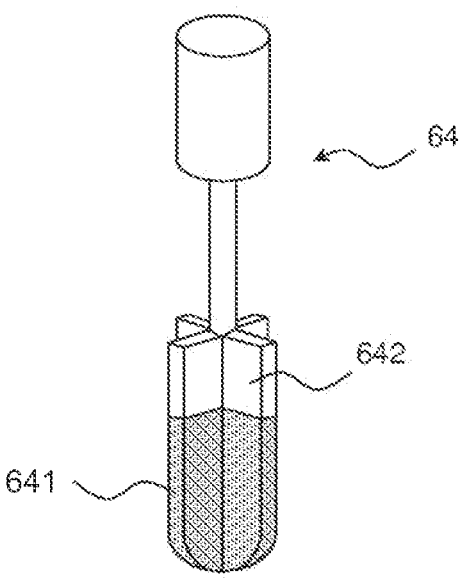
FIG. 10 is a schematic depiction of the sensitised capture support, depicted in FIG. 8, after analysis which gave a positive result.

As detailed hereafter, the detection is carried out during the incubation period by immersing a capture support as described in FIG. 10, sensitised with three anti-*Listeria* spp. recombinant phage proteins in a closed container containing the sample, diluted in the reaction medium.

Protocol:

Step 1: Re-Suspension of the Samples in the Reaction Medium

All of the environmental samples are prepared as in the example detailed hereafter;

Sponges (8 cm×3 cm) used for taking surface samples are divided into two halves, treated as follows:

Sample 1: in a container (i.e. pillbox), the first 1/2 sponge is contaminated artificially by 5 CFU of a strain belonging to the genus *Listeria* and re-suspended in 45 mL of LX medium (bioMérieux, Ref. 42635) supplemented by 0.1 g/L of TTC (bioMérieux, Ref. 04568088);

Sample 2: in a second container (i.e. pillbox), the other half which is not contaminated by a strain belonging to the genus *Listeria* is re-suspended in 45 mL of LX medium (bioMérieux, Ref. 42635) supplemented by 0.1 g/L of TTC (bioMérieux, Ref. 04568088).

The link between the samples and the strains inoculated artificially is presented in table 3 below:

TABLE 3

| Sample No. | Inoculated strain |
| --- | --- |
| Sample A1 | *L. monocytogenes* 4b ATCC 19115 |
| Sample A2 | N/A |
| Sample B1 | *L. seeligeri* NSB 22460 |
| Sample B2 | N/A |
| Sample C1 | *L. welshimeri* 6a |
| Sample C2 | N/A |

Figure 9:
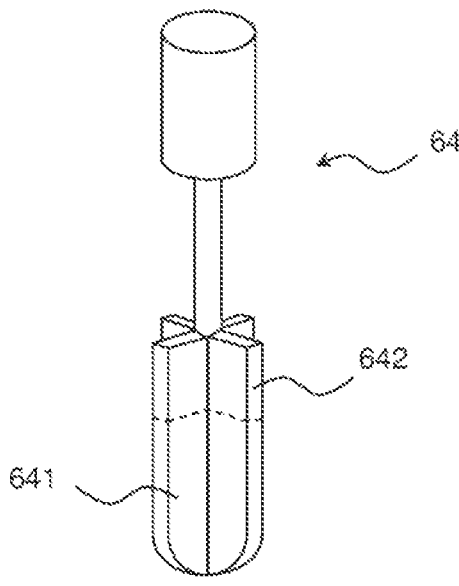
FIG. 9 is a schematic depiction of a sensitised capture support.

Step 2: Immersion of the Sensitised Support in the Container (Pillbox) Before Incubation A sensitised support, such as described in FIGS. 9 and 10 is placed in each pillbox. To do this, a hole is made in the pillbox lid such that the sensitised capture support 64 can be inserted forcibly until the analysis area (areas 641 and 642) is completely immersed in the culture medium. The pill boxes are then sealed with their stopper and incubated in an incubator at 30° C. for 24-48 h.

Step 3: Reading the Capture Supports at the End of the Incubation Period

At the end of incubation (24-48 h at 30° C.) and following the non-specific reduction of the TTC by all of the bacteria present in the sample (i.e. belonging to the annex flora and the target flora), the reaction medium is red in colour. Also in order to be able to observe the sensitised capture support which reveals the positivity or negativity of the analysed sample, the homogenisation bags are inclined in order to isolate the sample from the reaction medium. Each sample is also analysed by the VIDAS® LIS (Ref. 30700) method.

The results obtained are listed in Table 4 below:

TABLE 4

| Sample No. | Inoculated strain | Optical Biosensor Result | VIDAS LIS Result |
| --- | --- | --- | --- |
| Samp. A1 | *L. monocytogenes* 4b ATCC 19115 | + | + |
| Samp. A2 | N/A | − | − |
| Samp. B1 | *L. seeligeri* NSB 22460 | + | + |
| Samp. B2 | N/A | − | − |
| Samp. C1 | *L. welshimeri* 6a | + | + |
| Samp. C2 | N/A | − | − |

For the sensitised capture support, a red coloration of area 641 and an absence of coloration of area 642 of the capture support highlight the positivity of the sample (see FIG. 10).

In accordance with the experimental plan, the 1 samples are positive, whereas the 2 samples versus negatives are negative. The analysis of these same samples by the VIDAS LIS method led to similar results, thus confirming the results obtained via optical reading of a sensitised capture support.

Example 7: Elaboration of the Particles Functionalised (Conjugated) by at Least One Binding Partner Specific to the Target Microorganism For this example, two types of conjugates are elaborated from latex particles of 400 nm in diameter.

Preparation by adsorption of the specific binding partner (anti-*E. coli* O157: H7 recombinant phage protein) following the steps below:

1. washing the latex particles (Plain Hidye blue, Polymer lab) in VERSOL water by centrifuging;

2. adsorption of the specific binding partners at 150 µg/mL in phosphate buffer pH 7 in the presence of the latex particles at a solid content of 0.5% for 3 hours at ambient temperature and with wheel agitation.

The adsorption yields are greater than 80%, it is therefore not necessary to wash the latex particles after adsorption.

Preparation by coupling the specific binding partner (anti-O157 recombinant phage protein) following the steps below:

1. washing the latex particles (Carboxylic Hidye, Polymer lab) in versol water by centrifuging;

2. coupling to ethyl-(N',N'-dimethylamino) propylcarbodiimide hydrochloride (EDC) of 125 µg/mL streptavidine in 20 mM phosphate buffer pH 7 in the presence of the latex particles at a solid content of 0.5% by agitation in a thermomixer at 37° C. and 700 rpm for 3 hours;

3. the uncoupled streptavidin is eliminated by 20 minutes of centrifugation at 5000 g and the remainder is taken back up in 20 mM Tris buffer pH 7;

4. addition of the 150 µg/mL biotinylated specific binding partner (anti-*E. coli* O157: H7 biotinylated recombinant phage protein) and incubation for 3 hours at ambient temperature with wheel agitation;

5. elimination of the excess of binding partner by centrifugation for 10 minutes at 7000 g and taken back up in 20 mM Tris buffer pH 7.

Example 8: Detection of *Escherichia coli* O157: H7 in Food Samples Via the Agglutination of Sensitised Latex Particles in Liquid Media The aim of this experiment is to directly detect, via the agglutination of sensitised blue latex particles such as described in the preceding example, the presence of the target bacteria *E. coli* O157: H7 in a food sample during enrichment.

As detailed hereafter, the detection is carried out during the incubation period by immersing the sensitised blue latex particles with an anti-*E. coli* O157: H7 recombinant phage protein, in the closed container which contains the food sample, diluted in the enrichment medium.

Protocol:

Step 1: Re-Suspension/Dilution of the Samples in the Enrichment Medium

Six samples are prepared as follows:

Sample A1: in a homogenisation bag, 25 mL of pasteurised milk contaminated by CFU of *E. coli* O157: H7 are diluted in 225 mL of BPW (bioMérieux, ref. 42043);

Sample A2: in a homogenisation bag, 25 mL of pasteurised milk not contaminated by *E. coli* O157: H7 are diluted in 225 mL of BPW;

Sample B1: in a homogenisation bag, 25 g of salmon contaminated by 5 CFU of *E. coli* O157: H7 are re-suspended in 225 mL of BPW;

Sample B2: in a homogenisation bag, 25 g of salmon not contaminated by *E. coli* O157: H7 are re-suspended in 225 mL of BPW;

Sample C1: in a homogenisation bag, 25 g of salad contaminated by 5 CFU of *E. coli* O157: H7 are re-suspended in 225 mL of BPW;

Sample C2: in a homogenisation bag, 25 g of salad not contaminated by *E. coli* O157: H7 are re-suspended in 225 mL of BPW;

Three repetitions were carried out for each sample.

Step 2: Insertion of the Tube Containing the Reaction Medium into the Homogenisation Bag Prior to Incubation In accordance with FIG. 11, a tube containing the reaction medium is then added into the homogenisation bag. The reaction medium is composed of 100 µl of sensitised blue latex particles and 1.4 mL of BPW supplemented by 10 mg/L of vancomycin.

The homogenisation bags are then re-closed by means of a closing pin and placed in a programmable incubator for a three-phase incubation. In fact, the transfer of an aliquot of the sample (0.5 mL) from the homogenisation bag to the tube containing the reaction media is performed in accordance with the process described in document WO-A-2004/092401, based on the law of perfect gases (pV=nRT).

The incubation period is divided as follows:

Phase 1:16 h at 41.5° C.; enrichment of the 25 g sample diluted in BPW,

Phase 2:1 h at 30° C.; transfer of 0.5 mL of sample into the tube containing the reaction medium, Phase 3:8 h at 1.5° C.; enrichment of the reaction medium containing the 0.5 mL aliquot, According to the experimental plan, the Samp. No. 1 samples were determined as positive versus negative for the Samp. No. 2 samples. The analysis of these same samples by the VIDAS ECPT method led to similar results, thus confirming the results obtained via the agglutination of sensitised latex particles in liquid medium.

---

The invention claimed is:

1. A process of detecting at least one microorganism present in a sample placed in a closed container, the process comprising:

a) placing the sample in the container in contact with:
      a culture medium,
      a revealing system capable of allowing the detection, and
      a support capable of capturing the microorganism(s) to be detected, the support comprising magnetic particles,
   b) closing the container,
   c) placing the container under conditions capable of allowing growth of the microorganism(s),
   c') transferring all or part of a mixture comprising sample, the culture medium, and the support capable of capturing the microorganism(s) to be detected and potentially the revealing system, from the container to at least one second container,
   d) applying a magnetic field to the magnetic particles for bringing together the magnetic particles, and
   e) detecting in real-time inside the closed container, using a detection means, the presence of the microorganism(s) fixed onto the capture support.

2. The process according to claim 1, wherein at least one specific or non-specific binding partner of the microorganism(s) is fixed onto the magnetic particles.

3. The process according to claim 2, wherein the specific binding partner is selected from the group consisting of antibodies, Fab fragments, Fab' fragments, recombinant or non-recombinant phage proteins, and phages.

4. The process according to claim 1, further comprising confirming the detection of the microorganism(s) in a step f).

5. The process according to claim 4, wherein the confirming in step f) is accomplished using a detection means that is identical to or different from the detection means used for the detection in step e).

6. The process according to claim 1, wherein the detection means is selected from the group consisting of: an electrical detection means, an electrochemical detection means, an optical detection means, an acoustic detection means, a thermal detection means, a mechanical detection means, and a magnetic detection means.

7. The process according to claim 1, wherein the detection means is an electrical detection means, an electrochemical detection means, or an optical detection means.

8. The process according to claim 1, wherein the detection means is a Raman spectrometer.

9. The process according to claim 1, wherein the support for capturing the microorganism(s) also constitutes the detection means.

10. The process according to claim 1, wherein the application of the magnetic field is repeated.

11. The process according to claim 1, wherein the container is a homogenisation bag, a flask, a bottle, or a pillbox.

12. The process according to claim 1, wherein the detection means is connected to a data analysis system.

13. The process according to claim 12, wherein the connection between the capture support or the detection means and the data analysis device system is a wired connection or a wireless connection.

14. The process according to claim 1, wherein the sample is a food sample, a biological sample, or an environmental sample.

15. The process according to claim 1, wherein the detection in step e) is demonstrated by an appearance of real-time agglutination of the magnetic particles.

* * * * *